(12) United States Patent
Da Silva et al.

(10) Patent No.: US 7,697,738 B2
(45) Date of Patent: Apr. 13, 2010

(54) CALIBRATION IMAGE ALIGNMENT IN A PET-CT SYSTEM

(75) Inventors: Angela J. Da Silva, Danville, CA (US); Zuo Zhao, Mountain View, CA (US)

(73) Assignee: Koninklijke Philips electronics N.V., Eindhoven (NL)

( * ) Notice: Subject to any disclaimer, the term of this patent is extended or adjusted under 35 U.S.C. 154(b) by 1087 days.

(21) Appl. No.: 10/569,190

(22) PCT Filed: Aug. 6, 2004

(86) PCT No.: PCT/IB2004/002634

§ 371 (c)(1),
(2), (4) Date: Feb. 22, 2006

(87) PCT Pub. No.: WO2005/018456

PCT Pub. Date: Mar. 3, 2005

(65) Prior Publication Data

US 2008/0212859 A1     Sep. 4, 2008

Related U.S. Application Data

(60) Provisional application No. 60/497,651, filed on Aug. 25, 2003.

(51) Int. Cl.
*G06K 9/00* (2006.01)
(52) U.S. Cl. .................................... 382/128
(58) Field of Classification Search .......... 382/128–134; 128/920–930; 250/455–465; 356/39–49; 600/407, 411, 415, 427
See application file for complete search history.

(56) References Cited

U.S. PATENT DOCUMENTS 5,469,847 A * 11/1995 Zinreich et al. ............. 600/414

(Continued)

FOREIGN PATENT DOCUMENTS

EP      1 413 251 A1    4/2004

(Continued)

OTHER PUBLICATIONS

Townsend, D.W., et al.; A combined PET/CT scanner: the path to true image fusion; 2002; British Journal of Radiology; 75:S24-S30.

(Continued)

*Primary Examiner*—Samir A Ahmed
*Assistant Examiner*—Atiba O Fitzpatrick

(57) ABSTRACT

A phantom (44) is used to calibrate a multi-modality imaging system (10) that includes a nuclear imaging system (12) and a CT scanner (14). The phantom (44) includes marker receiving cavities (96) positioned at fixed locations in the phantom, in which markers (46) are removably placed. The markers (46) include CT markers (90), which are imageable by the CT scanner (14), and radioisotope markers (48), which are imageable by the nuclear imaging system (12). The radioisotope markers (48) are disposed into wells (92) provided at a center of mass of each disk-like CT marker. The markers (46) have a label (94) identifying its isotope. The phantom (44), rigidly affixed to a couch (32), is imaged by the nuclear imaging system (12) and by the CT scanner (14). A transformation processor (72) calculates a transformation which brings centroids of the CT markers (90) in a CT image and the radioisotope markers (48) in a nuclear image into alignment.

21 Claims, 5 Drawing Sheets

U.S. PATENT DOCUMENTS

| | | | | |
|---|---|---|---|---|
| 5,565,684 | A | 10/1996 | Gullberg et al. | 250/363.04 |
| 5,672,877 | A | 9/1997 | Liebig et al. | 250/363.04 |
| 5,703,056 | A * | 12/1997 | Blasberg et al. | 514/44 R |
| 5,871,013 | A | 2/1999 | Wainer et al. | 128/653.1 |
| 6,205,347 | B1 * | 3/2001 | Morgan et al. | 600/407 |
| 6,328,700 | B1 * | 12/2001 | Rheinhardt et al. | 600/504 |
| 6,364,526 | B2 | 4/2002 | Ivan et al. | 378/198 |
| 6,419,680 | B1 | 7/2002 | Cosman et al. | 606/130 |
| 6,448,559 | B1 | 9/2002 | Saoudi et al. | 250/367 |
| 6,493,574 | B1 | 12/2002 | Ehnholm et al. | 600/429 |
| 2001/0004395 | A1 | 6/2001 | McCrory et al. | 378/162 |
| 2003/0212320 | A1 * | 11/2003 | Wilk et al. | 600/407 |

FOREIGN PATENT DOCUMENTS

| | | |
|---|---|---|
| WO | WO 00/75691 A1 | 12/2000 |
| WO | WO 02/34136 A2 | 5/2002 |
| WO | WO 03/025621 A1 | 3/2003 |
| WO | WO 03/040745 A1 | 5/2003 |

OTHER PUBLICATIONS

Philips "Positron Emission Tomography" GEMINI™ http://www.medical.philips.com/main/products/pet/products/gemini/index.html.

Siemens "Biograph Sensation 16" http://www.siemensmedical.com/webapp/wcs/stores/servlet/CategoryDisplay?storeID= 10001&1.

Siemens "Nuclear Medicine/PET—biograph PET/CT Systems" http://www.siemensmedical.com/sebapp/wcs/stores/servlet/CategoryDisplay?storeID-1001.

GE Medical Systems "GE PET and CT Imaging in a Single System" http://www.gemedicalsystems.com/rad/nm_pet/products/pet_sys/petctl.html.

* cited by examiner

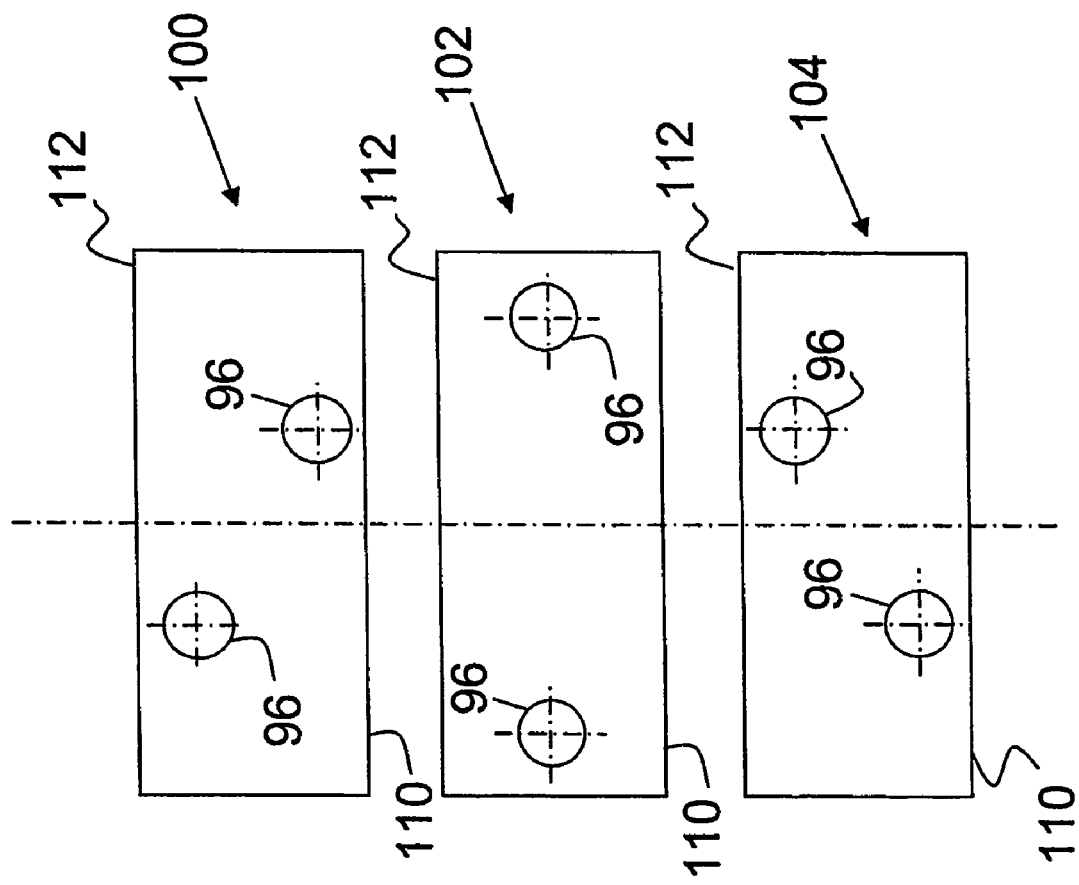

CALIBRATION IMAGE ALIGNMENT IN A PET-CT SYSTEM

CROSS REFERENCE TO RELATED APPLICATIONS

This application claims the benefit of U.S. provisional application Ser. No. 60/497,651 filed Aug. 25, 2003, which is incorporated herein by reference.

The present invention relates to the diagnostic imaging systems and methods. It finds particular application in conjunction with multi-modality systems such as the GEMINI™ PET-CT system manufactured by Philips. It will be appreciated that the invention is also applicable to the combination of SPECT and CT scanners, and the like combinations.

In multi-modality tomographic systems, two or more different sensing modalities are used to locate or measure different constituents in the object space. In the PET-CT system, the PET creates images of high metabolic activity in the body, rather than creating images of surrounding anatomy. CT scans allow doctors to see the internal structures within the human body. Before having a PET-CT scan, the patient receives a dose of a radiopharmaceutical. The pharmaceutical concentrates in a particular organ or region and causes radiation to be emitted from this organ or region. During the scan, tracings of the emitted radiation are detected by the system creating an image of the distribution of the radiopharmaceutical in the patient. The image can show the circulatory system and/or the relative absorption of the radiopharmaceutical in various regions or organs. Integration of the anatomical data from the CT scan with the metabolic data from the PET scan in the PET-CT image gives physicians visual information to determine if disease is present, the location and extent of disease and track how rapidly it is spreading. The PET-CT system is particularly helpful in difficult-to-treat regions (e.g. head & neck area, mediastinum, postsurgical abdomen) and localization of the treatment area for the patients receiving radiation therapy or chemotherapy.

The most significant problem in the multi-modality imaging systems is image registration. In the GEMINI™ PET-CT scanner, patients requiring both procedures undergo a CT scan immediately followed by a PET scan while positioned in the same scanning bed. Although positioning the patient in the same position for both exams by moving the patient a known longitudinal distance reduces the possibility of misregistration of the CT and PET images, there remains the possibility of misregistration due to mechanical misalignments between the two imaging spaces, aging of the imaging systems, and the like. Furthermore, since one image (e.g., CT) may be used to correct the other image (e.g., attenuation correction of PET or SPECT using a CT generated attenuation map), such misregistrations can affect overall image quality as well as registration of the two images.

There is a need for a calibration technique, which is simple and easy to perform, to compensate for static misalignment between the PET and CT imaging spaces. The present invention provides a new and improved imaging apparatus and method which overcomes the above-referenced problems and others.

In accordance with one aspect of the present invention, a system for calibrating a multi-modality imaging apparatus is disclosed. The system includes a phantom that receives markers. The markers include CT markers, which are imageable by a CT scanner and positioned at fixed locations in the phantom, and radioisotope markers, which are imageable by a nuclear imaging system. A means determines a transformation that brings the CT markers in a CT image and radioisotope markers in a nuclear image into alignment.

In accordance with another aspect of the present invention, a method of aligning a nuclear imaging system and a CT scanner in a multi-modality imaging system is disclosed. Markers are received in a phantom. The markers include CT markers, which are imageable by the CT scanner and positioned at fixed locations in the phantom, and radioisotope markers, which are imageable by the nuclear imaging system. A transformation, which brings the CT markers in a CT image and radioisotope markers in a nuclear image into alignment, is determined.

One advantage of the present invention resides in improving the overall image quality and image registration by reducing alignment errors attributable to the mechanical misalignment of scanners.

Another advantage of the present invention resides in providing a fast and convenient way of aligning and recalibrating scanners in multi-modality systems.

Yet another advantage of the present invention resides in providing a calibration phantom with interchangeable markers.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

FIG. 5A is a diagrammatic illustration of a top plate of the calibration phantom;

FIG. 5B is a diagrammatic illustration of a middle plate of the calibration phantom;

FIG. 5C is a diagrammatic illustration of a bottom plate of the calibration phantom.

Figure 1:
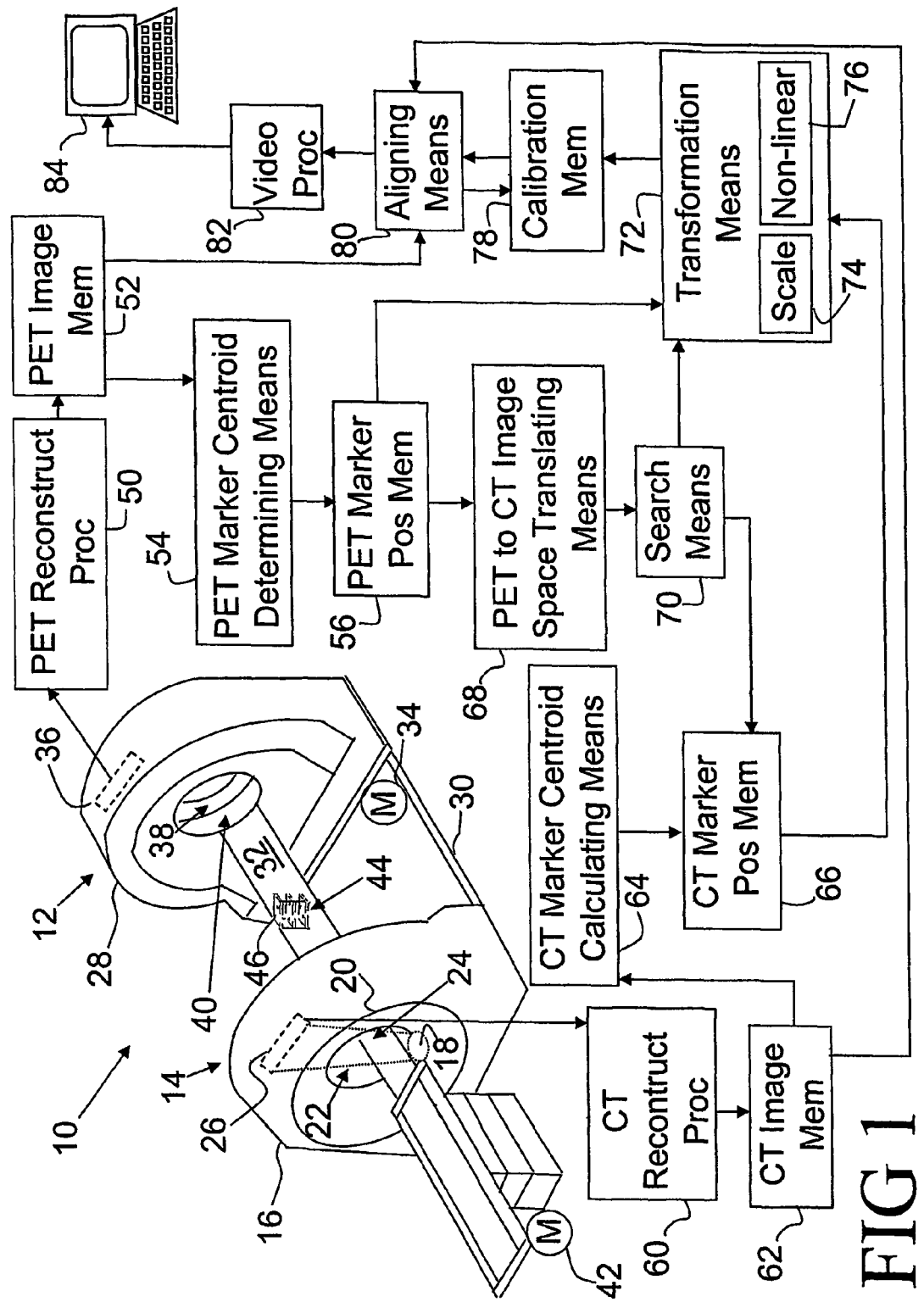
FIG. 1 is a diagrammatic illustration of a calibration system in accordance with the present invention.

With reference to FIG. 1, a multi-modality system 10 includes a nuclear imaging system 12 and a computed tomography (CT) scanner 14. The CT scanner 14 includes a non-rotating gantry 16. An x-ray tube 18 is mounted to a rotating gantry 20. A bore 22 defines an examination region 24 of the CT scanner 14. An array of radiation detectors 26 is disposed on the rotating gantry 20 to receive radiation from the x-ray tube 18 after the x-rays transverse the examination region 24. Alternatively, the array of detectors 26 may be positioned on the non-rotating gantry 16.

Figure 2:
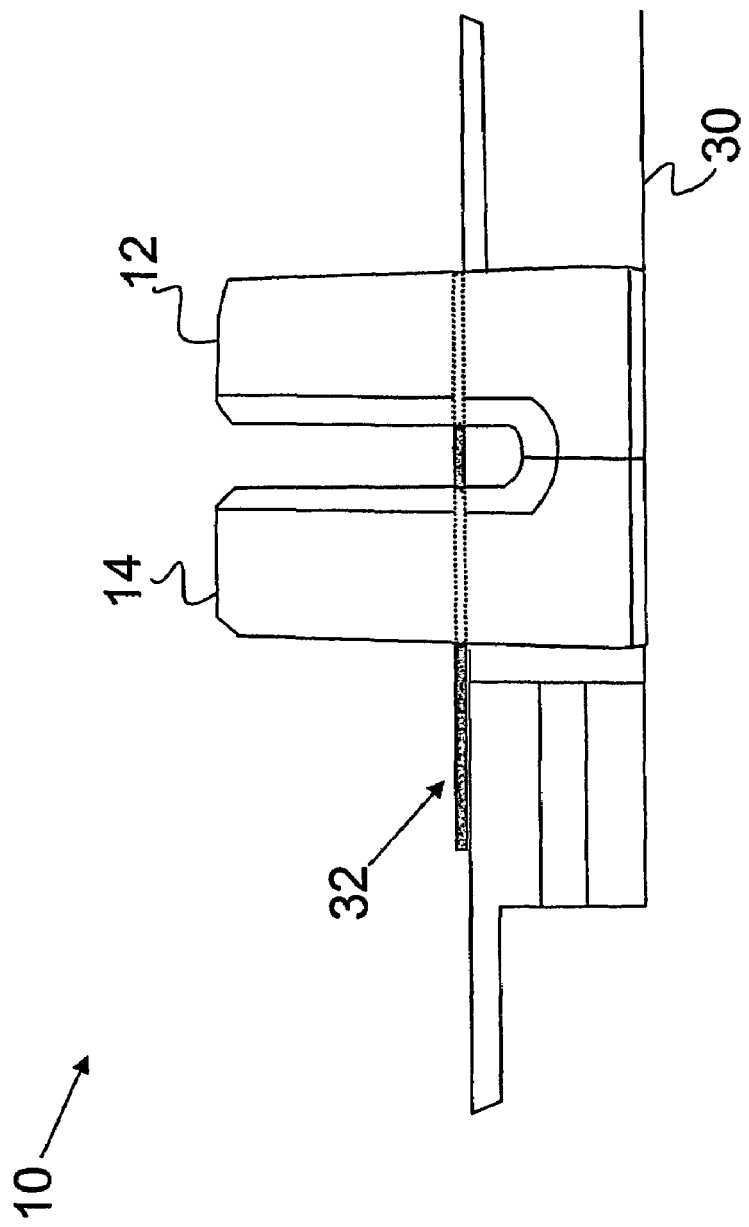
FIG. 2 is a diagrammatic illustration of a multi-modality imaging system in a closed position.

The nuclear imaging system 12 preferably includes a positron emission tomography (PET) scanner 28 which is mounted on tracks 30. Of course, SPECT and other nuclear imaging systems are also contemplated. The tracks 30 extend in parallel to a longitudinal axis of a subject support or couch 32, thus enabling the CT scanner 14 and PET scanner 28 to form a closed system as seen in FIG. 2. A moving means 34, such as a motor and a drive, is provided to move the scanner 28 in and out of the closed position. Detectors 36 are arranged around a bore 38 which defines an examination region 40. In the PET system, the detectors 36 are preferably arranged in a stationery ring, although rotatable heads are also contemplated. In the SPECT system, the detectors 36 are preferably incorporated into individual heads, which are mounted for rotational and radial movement relative to the patient. A couch moving means 42, such as a motor and a drive, provides a longitudinal movement and vertical adjustment of the couch 32 in the examination regions 24, 40.

With continuing reference to FIG. 1, a phantom 44, including CT-nuclear markers 46, is rigidly attached to the couch 32. As illustrated in FIG. 3B, each marker 46 includes a vial 48 of a radioisotope. For PET, the isotope is a positron emitter; for SPECT, the isotope is a photon emitter. The couch 32 with the phantom 44 is moved by the couch moving means 42 into the examination region 40 for a 3D image to be generated by the PET scanner 28. Electronic data is reconstructed into a PET image by a PET reconstruction processor 50 and stored in a PET image memory 52. A centroid determining program or means 54 finds coordinates of a center of mass of each radioisotope marker 48. The coordinates are stored in a radioisotope marker position memory 56.

The couch moving means 42 moves the couch 32 to position the phantom 44 in the CT scanner examination region 24, where the CT image is taken. More particularly, the phantom 44 is moved to the position in the CT examination 24 region that is geometrically and mechanically predicted as being the same as its imaged position in the PET imaging region. Electronic data is reconstructed into a 3D CT image by a CT reconstruction processor 60 and stored in a CT image memory 62. A CT marker centroid calculating means 64 calculates coordinates of a center of mass for each CT-nuclear marker 46. The CT markers' centroid positions are stored in a CT marker position memory 66. The radioisotope markers position coordinates, previously calculated for the PET image, are translated into CT image space by a PET to CT space image translating processor or means 68 using the known geometry and mechanical alignment of the PET and CT scanners. A CT marker search processor or means 70 retrieves the radioisotope markers position information and looks in the CT marker position memory 66 for the coordinates of the corresponding markers. More specifically, the search means 70 goes to the coordinate locations in the CT marker position memory 66 that correspond to the PET locations to see if the CT-nuclear marker centroids overlay the radioisotope PET markers 48, i.e., to see if they are aligned. If the PET and CT markers are not aligned, the search means 70 moves from the corresponding CT coordinate position outward in generally concentric spheres until the locations of the corresponding CT marker centroids is identified. A transformation processor or means 72 receives the coordinates of the corresponding markers and determines the amount of linear shift and rotation to bring the PET image and the CT image into precise alignment, i.e., such that the center of mass points from the CT marker image overlie the center of mass points in the PET marker image. Alternatively, the transformation means 72 may include a scaling algorithm or means 74 or non-linear distortion correction algorithm or means 76. The transformation parameters, determined by the transformation means 72, are stored in a calibration memory 78 and are used by an aligning processor or means 80 to align PET and CT images with each other in the subsequent scans. A video processor 82 processes the received data for a display on a monitor 84.

Figure 3A:
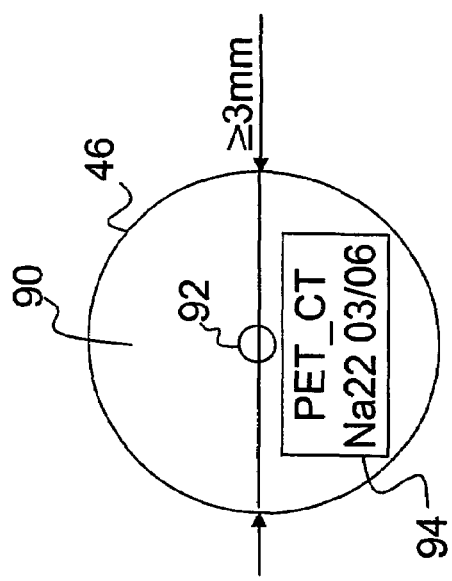
FIG. 3A is a diagrammatic illustration of a top view of a nuclear-CT marker.
Figure 3B:
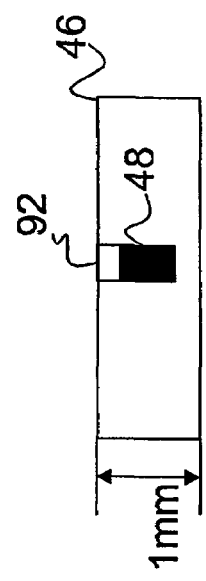
FIG. 3B is a diagrammatic illustration of a side view of a nuclear-CT marker.
Figure 3C:
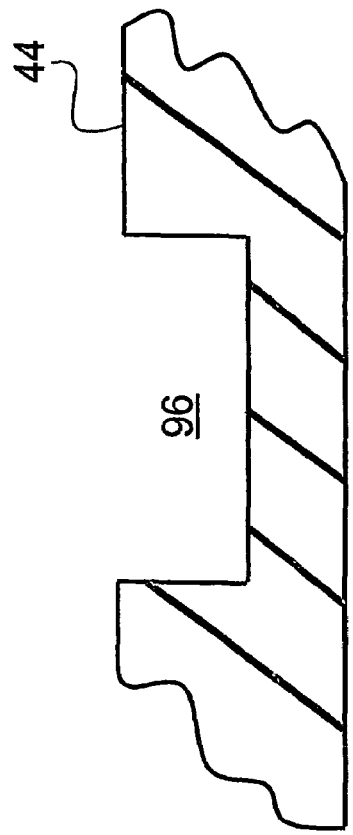
FIG. 3C is a diagrammatic illustration of a side view of a portion of a holder or phantom.

With reference to FIGS. 3A-C, each CT-nuclear marker 46 includes a disc 90 of dense, CT imageable material with a well 92 positioned in its center, which contains the radioisotope marker 48. Typically, the radioisotope marker 48 is the vial containing an isotope with a relatively long half-life, preferably of more than 100 days, to prevent frequent replacements. For the PET-CT combination, a preferential isotope is Na-22 with a half-life of 2.6 years. However, isotopes with shorter half-lives such as Ge-68 might be used as well. For the SPECT-CT combination, the isotope for the radioisotope marker 48 is selected from the isotopes having a half-life more than 100 days and a strong energy peak between 50 keV and 600 keV. Examples of appropriate SPECT imageable isotopes are Co-57, Gd-153, Cd-109, Ce-139, Am-241, Cs-137 and Ba-133. Preferably, the well 92 of each CT-nuclear marker 46 is permanently filled with the appropriate isotope and sealed at the manufacturing site. Each marker 46 is clearly labeled with a label 94 to identify the isotope it carries within, and, optionally, its expiration date. Optionally, the discs 90 are color coded to differentiate SPECT and PET markers.

With continuing reference to FIG. 3C, the CT-nuclear marker 46 is placed into a well or cavity 96 of a corresponding size in the phantom 44. The disc 90 is composed of a material having a good contrast in the CT image as compared to the phantom 44. Typically, the phantom is constructed from an acrylic material, although other materials with lower CT numbers might be used. The disc 90 might be constructed of glass-filled Teflon or other suitable material, having a significantly different CT number from the phantom, to be readily identified during the CT scan. In the preferred embodiment, the disc 90 is a disc of about 5 mm thick and 25 mm in diameter to allow a better accuracy of calibration. Smaller discs might be used provided sufficient sampling of the disk 90 occurs during the imaging process; a minimum diameter of 3 mm allows spanning at least three 1 mm slices. Rather than the disc, the CT-nuclear marker 46 might be a cylinder, cube, or other structure.

Figure 4:
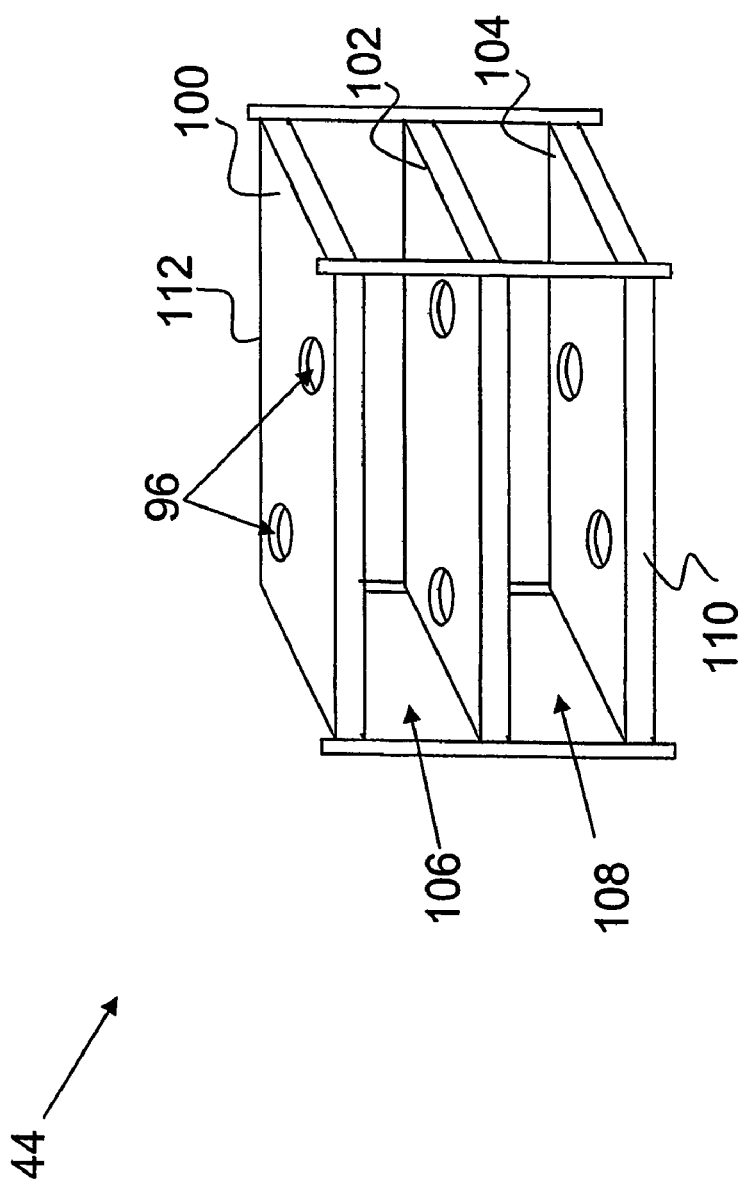
FIG. 4 is a diagrammatic illustration of a calibration phantom.

With reference to FIG. 4, in the preferred embodiment, the phantom 44 includes a top layer 100, a middle layer 102 and a bottom layer 104, each with two marker receiving cavities 96. The top and middle layers 100, 102 define a first air gap 106. The middle and bottom layers 102, 104 define a second air gap 108. Each of the layers 100, 102, 104 includes a front side 110 and a back side 112. The CT-nuclear markers 46 are placed in the cavities 96 and held in place by gravity. In order to calibrate the CT-SPECT system, the CT-PET markers containing the PET imageable isotope are replaced by the CT-SPECT markers, containing the SPECT imageable isotope.

With reference to FIGS. 5A-C, the centers of the cavities 96 are positioned such that no three cavities are in a line, yet still span and are distributed around the CT and nuclear imaging regions. This enables offset and rotation translations about three orthogonal axes to be determined from only six markers. Of course, the phantom can be designed to accept a larger number of markers.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

Having thus described the preferred embodiments, the invention is now claimed to be:

1. A system for calibrating a multi-modality imaging apparatus comprising:
   a phantom which includes cavities in which markers are removably placed and held in place by gravity at fixed locations in the phantom, which markers include:
   a CT marker, which is imageable by a CT scanner, and
   a radioisotope marker, which is imageable by a nuclear imaging system; and
   a processor programmed to determine a transformation which brings the CT markers in a CT image and radioisotope markers in a nuclear image into alignment.

2. The system as set forth in claim 1, wherein the radioisotope markers are affixed at centroids of the CT markers and the processor is further programmed to:

determine a centroid of each CT marker in the CT image, the transformation means aligning the centroids of the CT markers and the radioisotope markers.

3. The system as set forth in claim 2, wherein the processor is further programmed to:
   translate the coordinates of the radioisotope markers from nuclear image space into CT image space; and
   locate coordinates of a closest CT marker centroid to the coordinates of the corresponding radioisotope marker, the transformation determining means determines the transform which brings the CT marker centroid coordinates and the radioisotope marker coordinates into coincidence.

4. The system as set forth in claim 1, wherein each radioisotope marker includes an isotope disposed in a well positioned at a center of mass of an associated one of the markers.

5. The system as set forth in claim 4, wherein the isotope has a half-life of more than 100 days.

6. The system as set forth in claim 1, further including:
   a nuclear imager which generates a 3D image representation of the radioisotope markers;
   a CT scanner which generates a 3D image representation of the CT markers; and
   a patient support to which the phantom is mountable to move the phantom between the nuclear imager and the CT scanner.

7. The system as set forth in claim 6, wherein the processor is further programmed to align subsequently generated 3D image representations of a subject generated by the nuclear imager and the CT scanner into alignment using the transform determined by the determined transform.

8. The system as set forth in claim 6, wherein the nuclear imager is a PET scanner and the radioisotope marker includes an isotope from a group consisting of Na-22 and Ge-68.

9. The system as set forth in claim 6, wherein the nuclear imager is a SPECT scanner and the radioisotope marker includes an isotope from a group consisting of Co-57, Gd-153, Cd-109, Ce-139, Am-241, Cs-137 and Ba-133.

10. The system as set forth in claim 1, wherein the phantom further includes:
    a top layer;
    a middle layer secured underneath the top layer with a first air gap defined between the top and middle layers; and
    a bottom layer secured underneath the middle layer with a second air gap defined between the middle and bottom layers;
    each layer defining at least one marker receiving cavity.

11. The system as set forth in claim 10, wherein the CT markers are constructed of a material having a CT number substantially different from a CT number of the top, middle and bottom layers.

12. The system as set forth in claim 1, wherein the CT markers each includes a disc of CT imageable material having a diameter of 25 mm and a radioisotope marker receiving well at its centroid.

13. A CT-nuclear marker for use in the system of claim 1, the marker including:
    a 3 to 25 mm disc of an x-ray imageable material, the disc defining a well at a centroid thereof; and
    a radioisotope which is imageable by a nuclear imaging system, which radioisotope is sealed in the well.

14. A method using the system as set forth in claim 1, comprising:
    placing the markers in the cavities in the phantom;
    determining the transformation which brings the CT markers in a CT image and radioisotope markers in a nuclear image into alignment; and
    aligning images of a subject from the nuclear imaging system and images of the subject from the CT scanner in accordance with the determined transform.

15. The system comprising:
    a phantom for calibrating a multi-modality imaging apparatus, the phantom including a phantom frame which removably and interchangeably receives markers at pre-defined locations, each of the markers including:
    a portion which is radioopaque to be imageable by a CT scanner;
    a radioisotope fixedly disposed in a predetermined location in the radioopaque portion, which radioisotope emits radiation that is detected by at least one of a PET or SPECT scanner; and
    a label identifying at least one of:
    the isotope disposed within the marker,
    an expiration date of the contained isotope, and
    whether the marker is for use with PET or SPECT scanner.

16. The system as set forth in claim 15, wherein the phantom frame includes:
    a top layer;
    a middle layer secured underneath the top layer with a first air gap defined between the top and middle layers; and
    a bottom layer secured underneath the middle layer with a second air gap defined between the middle and bottom layers;
    each layer defining at least one marker receiving structure.

17. The system as set forth in claim 15, wherein the phantom includes cavities at the pre-defined locations in which the markers are removably held in place by gravity.

18. The system as set forth in claim 15, wherein the label identifies the isotope, the expiration date, and whether the marker is for use with a PET or SPECT scanner.

19. The system as set forth in claim 15, wherein the CT portion of the markers each includes a disc of CT imageable material having a diameter of 3-25 mm and a radioisotope receiving well at its centroid.

20. A method of using the system as set forth in claim 15, comprising:
    (a) placing a first set of the markers at the predefined locations of the phantom frame;
    (b) generating images of the first set of markers with a CT scanner and at least one of a PET or SPECT scanner; and,
    (c) from the images, determining a transform which aligns the markers in the CT image and the PET or SPECT image.

21. The method as set forth in claim 20, further including:
    removing the first set of markers and placing a second set of markers in the predefined locations; and
    repeating steps (b) and (c).

* * * * *